(12) United States Patent
Sandel et al.

(10) Patent No.: US 7,458,177 B2
(45) Date of Patent: Dec. 2, 2008

(54) MEDICATION MARKING SYSTEM

(75) Inventors: Dan Sandel, Chatsworth, CA (US); Lauren O. Baum, Chatsworth, CA (US)

(73) Assignee: Sandel Medical Industries LLC, Chatsworth, CA (US)

( * ) Notice: Subject to any disclaimer, the term of this patent is extended or adjusted under 35 U.S.C. 154(b) by 323 days.

(21) Appl. No.: 11/199,317

(22) Filed: Aug. 8, 2005

(65) Prior Publication Data

US 2005/0268505 A1  Dec. 8, 2005

Related U.S. Application Data

(62) Division of application No. 10/391,716, filed on Mar. 18, 2003, now Pat. No. 6,955,002.

(51) Int. Cl.
*G09F 3/10* (2006.01)
(52) U.S. Cl. .............. 40/638; 40/306; 40/310; 283/81
(58) Field of Classification Search ........... 40/638, 40/310, 324, 306; 283/81; 245/DIG. 3
See application file for complete search history.

(56) References Cited

U.S. PATENT DOCUMENTS

| | | | | |
|---|---|---|---|---|
| 3,037,310 A | * | 6/1962 | Montalto | 40/310 |
| 3,442,378 A | * | 5/1969 | Wolfe | 206/459.5 |
| 3,517,450 A | * | 6/1970 | Greco | 40/310 |
| 3,864,855 A | * | 2/1975 | Pekko et al. | 283/94 |
| 3,885,562 A | * | 5/1975 | Lampkin | 604/189 |
| 3,959,906 A | * | 6/1976 | Norris et al. | 40/595 |
| 4,195,734 A | | 4/1980 | Boner et al. | |
| 4,518,208 A | | 5/1985 | Marder | |
| 4,921,277 A | * | 5/1990 | McDonough | 283/81 |
| 4,976,351 A | | 12/1990 | Mangini et al. | |
| 5,046,609 A | | 9/1991 | Mangini et al. | |
| 5,692,640 A | * | 12/1997 | Caulfield et al. | 221/70 |
| 5,782,495 A | * | 7/1998 | Grosskopf et al. | 283/81 |
| 5,958,536 A | * | 9/1999 | Gelsinger et al. | 428/40.1 |
| 6,793,075 B1 | | 9/2004 | Jeter | |
| 2002/0017784 A1 | * | 2/2002 | Merry et al. | 283/81 |
| 2002/0056989 A1 | * | 5/2002 | Lewis-Leander | 283/81 |

* cited by examiner

*Primary Examiner*—Gary C Hoge
(74) *Attorney, Agent, or Firm*—Kenneth H. Ohriner; Perkins Coie LLP

(57) ABSTRACT

A flag for labeling drugs or medications provided in a medication cup, for use in the operating room, has a cup section with an adhesive back surface peelably attached to a backing sheet. A flag section is attached to the cup section of the flag at a bend line. A flag strip also having an adhesive back surface is supplied on the backing sheet. Multiple flags of different colors are preferably provided in a kit. A flag is attached to each cup. The flag section is labeled with a marker or a preprinted label, to indicate the content of the cup. The flag section is folded down so that it partially overlies the open top end of the cup. The syringe strip is adhered to a syringe used to draw medication out of the cup for administration to the patient. The flag and syringe strip provide a visual link or connection between each syringe and the contents of each cup. The risk of administering the wrong drug to a patient is reduced.

10 Claims, 3 Drawing Sheets

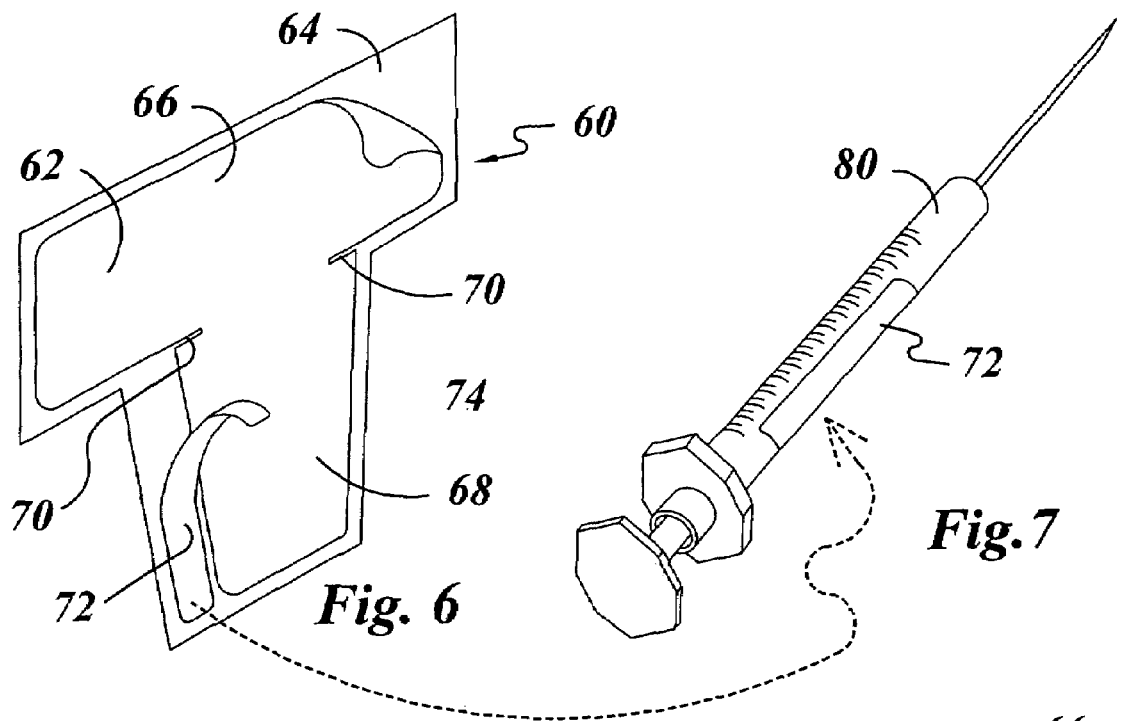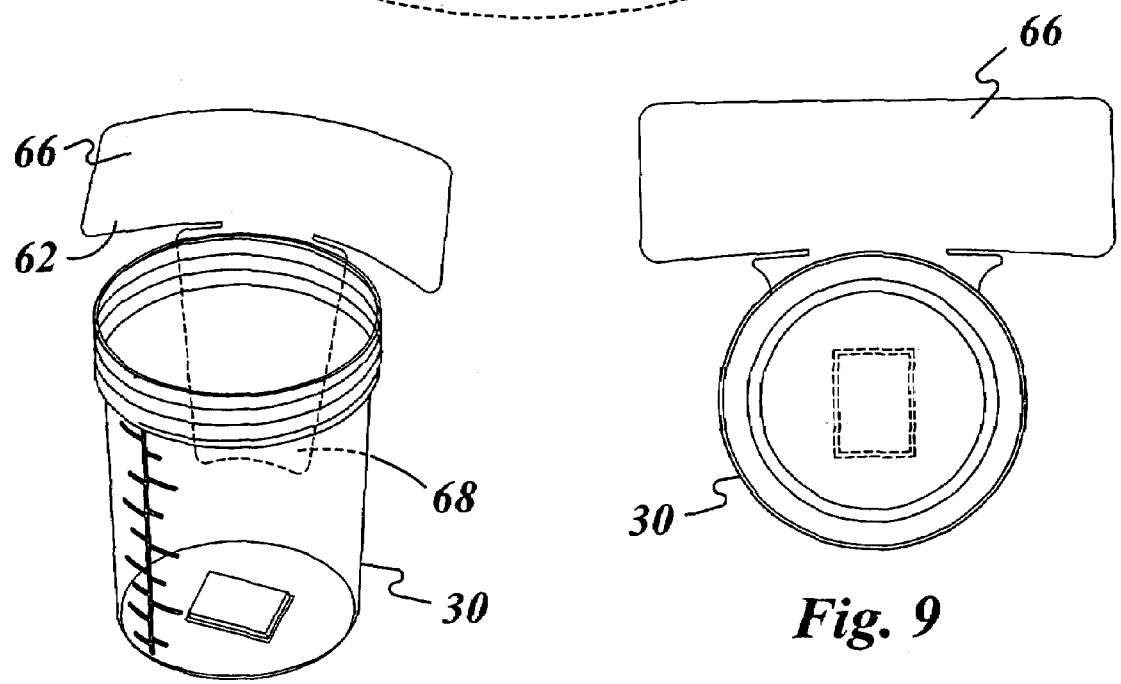

MEDICATION MARKING SYSTEM

PRIORITY CLAIM

This Application is a Divisional of U.S. patent application Ser. No. 10/391,716, filed Mar. 18, 2003, now U.S. Pat. No. 6,955,002 and incorporated herein by reference.

BACKGROUND OF THE INVENTION

Various studies have shown that hospital medication errors occur with alarming frequency, resulting in thousands of deaths and injuries each year. These medication errors most often involve omission of a prescribed drug, dispensing a drug not prescribed or intended, and providing improper dosages or improper administration of a prescribed medication. In one recent wide-ranging study by United States Pharmacopoeia analyzing medication mistakes at community, government, and teaching hospitals nationwide, thirteen percent of the total hospital medication errors involved administering the wrong drug. These types of errors occur in operating rooms, as well as in other hospital locations.

A still common practice in the operating room is to pour drugs into sterile cups. During surgery, the drugs are drawn into syringes for administration to the patient. It is, of course, critical that the correct drug be administered at the correct site, in the correct concentration and at the correct time, during a surgical procedure. For example, during a surgical procedure, Adrenalin may be poured into one cup, for delivery by a first syringe, and Lidocaine may be poured into a second cup for delivery via a second syringe. However, after these drugs are removed from their original containers and poured into the cups, it can be difficult to distinguish between them.

To better avoid administering the incorrect medication or drug, some hospitals have changed procedures by having certain drug vials fitted with caps that allow the medication to be drawn directly into the syringe. Another proposed solution is the use of pre-filled labeled unit doses. While these and other similar techniques can help to prevent giving the wrong drugs to a patient during surgery, disadvantages remain. Initially, these types of procedures have not necessarily been adopted in all hospitals. In addition, these types of procedures can be more difficult and time consuming to carry out, especially while maintaining the sterile field in the OR. These factors discourage using these types of procedures.

Consequently, notwithstanding the vast technical advances made in medicine, there is still a great need to reduce medication errors. This need is especially significant in the operating room (OR) environment.

SUMMARY OF THE INVENTION

In a first aspect, a medication labeling kit for use in an operating room includes one or more medication cups. A medication flag is attached to the medication cup. A marker may be provided for marking the medication flag, to indicate the medication provided into the medication cup.

In a second aspect, the medication flag has a flag section attached to a cup section at a bend line. The cup section has an adhesive back adapted to adhere to the outside cylindrical surface of the cup. The cup may be included with the kit or it may be separately provided. The cup may be reusable or disposable, and may be made of plastic, stainless steel, or other material. The flag, which may be foldable relative to the cup section, is easily visible to members of the surgical team, from virtually any viewing angle. Preferably, the medication flag is made of a colored transparent material. Different colored flags are preferably provided in the kit, for use with different medications. The flag can advantageously also be removed from the cup, without leaving any mark, residue or adhesive on the cup.

In a third aspect, one or more flag or syringe strips are provided with the medication marking flag. The syringe strip has an adhesive back surface, for attaching the strip onto a surgical tool or accessory, which will typically be a syringe. The syringe strip then provides a visual connection between the syringe and the cup. This helps the surgical team confirm the identification of the medication in the cup and syringe. The strip can also be written on to better label the syringe or other object.

In a method for labeling liquid medications, in an operating room environment, a medication flag is peeled off of a backing strip and adhered to the outside wall of a medication cup. This allows at least a part of the medication flag to be easily viewable by the surgical team, from virtually any viewing position. A syringe strip is preferably also peeled off the backing strip and applied to a medical instrument, such as a syringe, providing a visual link or connection between the medication cup and the syringe.

The invention resides as well in subcombinations of the system, kit, devices, and method steps described.

It is an object of the invention to provide an improved medication marking system, especially for use in an operating room. Other and further objects, features, and advantages will also become apparent from the following detailed description.

BRIEF DESCRIPTION OF THE DRAWINGS

In the drawings, wherein the same reference number indicates the same element in each of the views:

FIG. 6 is a front perspective view of a medication flag, as included in the kit shown in FIG. 1.

FIG. 7 is a perspective view of the flag or syringe strip shown in FIG. 6 applied to a syringe.

FIG. 8 is a perspective view of the medication flag shown in FIG. 6 applied to the medication cup shown in FIG. 3.

FIG. 9 is a top view of the medication cup and flag shown in FIG. 8.

DETAILED OF DESCRIPTION OF THE DRAWINGS

Figure 1:
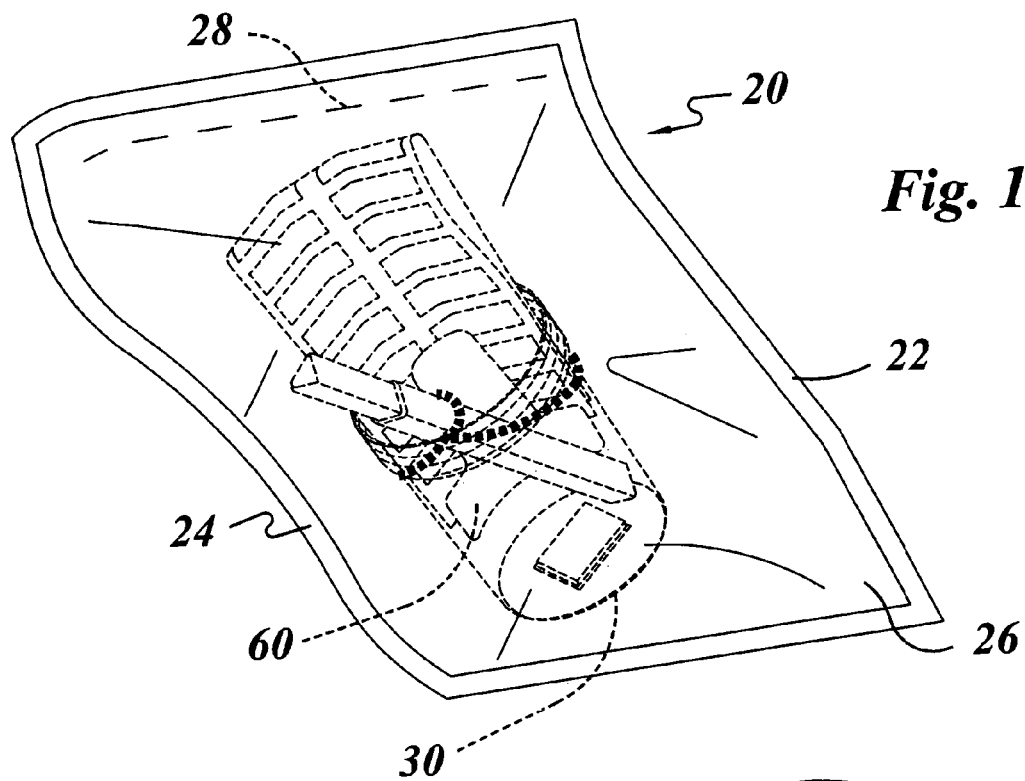
FIG. 1 is a perspective view of the present medication labeling kit.

Turning now in detail to the drawings, as shown in FIG. 1, a medication labeling kit contains one or more of the devices shown in FIGS. 2-6. The kit 20 includes a package or sterilization bag 22 having a flat preferably opaque back surface 24 joined to a preferably transparent concave front surface 26. The front and/or back surfaces 24 and 26 may have a perforation or tear line 28, to allow the package 22 to be easily opened. In general, after the kit is assembled and the package 22 is sealed, the kit is sterilized, using well known techniques. Consequently, notwithstanding later exposure to non-sterile conditions, the package 22 acts as a sterile barrier, maintaining the sterility on the contents of the kit. The kit may also be provided in a non-sterile condition for other applications.

Figures 2, 3:
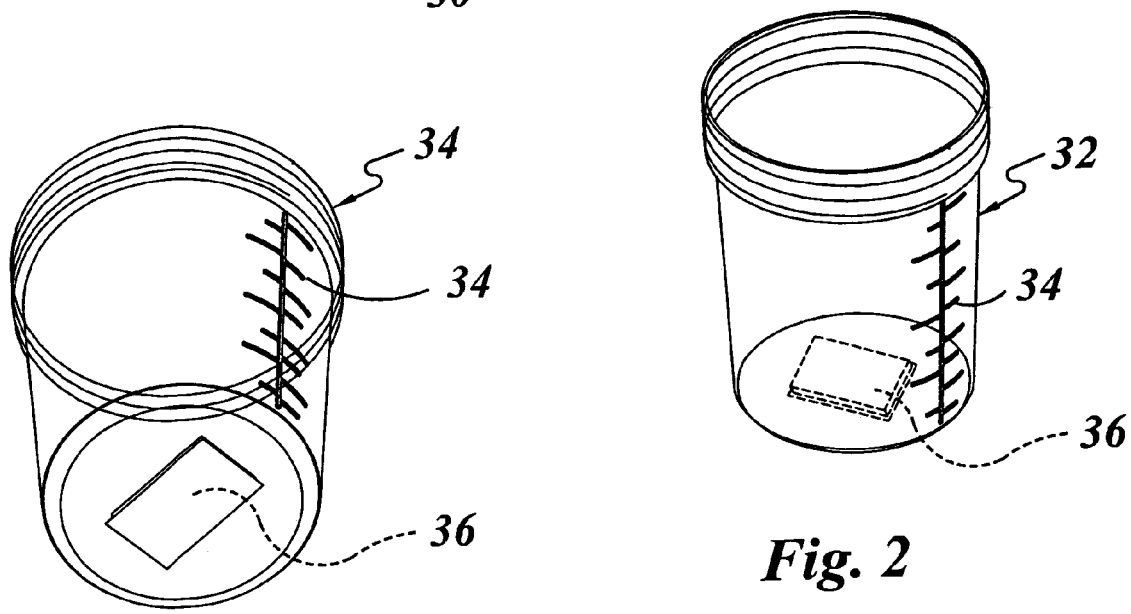
FIG. 2 is a perspective view of a medication cup, which may be provided in the kit shown in FIG. 1.
FIG. 3 is a perspective view of another medication cup, larger than the cup shown in FIG. 2, which may also be included in the kit shown in FIG. 1.

The kit may preferably include one or more disposable. Referring to FIGS. 2 and 3, a larger medication cup 30 and preferably also a smaller medication cup 32 are advantageously provided in the kit 20. Each cup preferably has volume markings 34 (e.g., in milliliters). An adhesive element, such as double-sided tape 36 is provided on the bottom of each cup. The tape is used to attach the cup onto a surgical drape, sheet, or other surface in the OR. The kit may be provided without any cups, allowing the package 22 to be more flat and compact.

Figure 4:
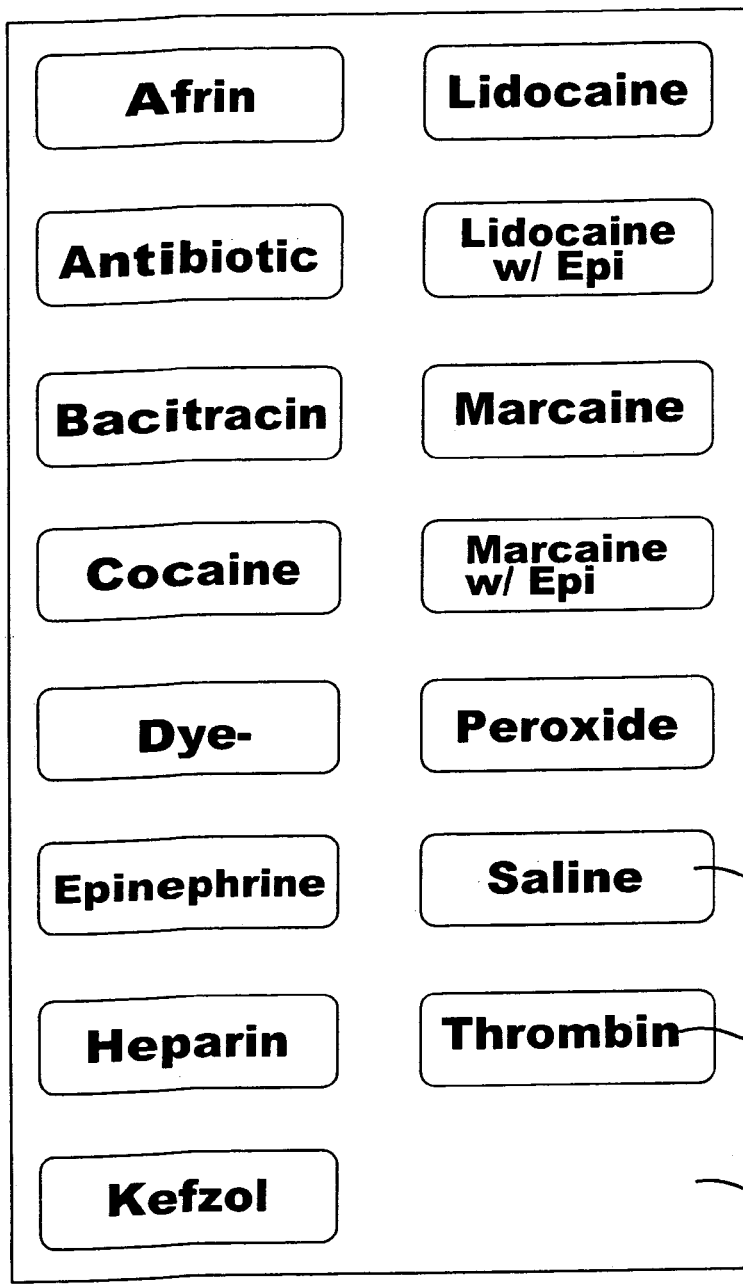
FIG. 4 is a front view of pre-printed medication labels on a peel-off backing strip, which may be included in the kit shown in FIG. 1.

Referring now to FIG. 4, preprinted medication labels 40 having an adhesive back surface are supplied on a peel-off backing sheet 42. Some or all of the labels 40 may have printed lettering 44, with the names of commonly used medications. Different kits may have different sets of preprinted labels which include labels printed with the names of medications commonly used for a specific surgical procedure.

Figure 5:
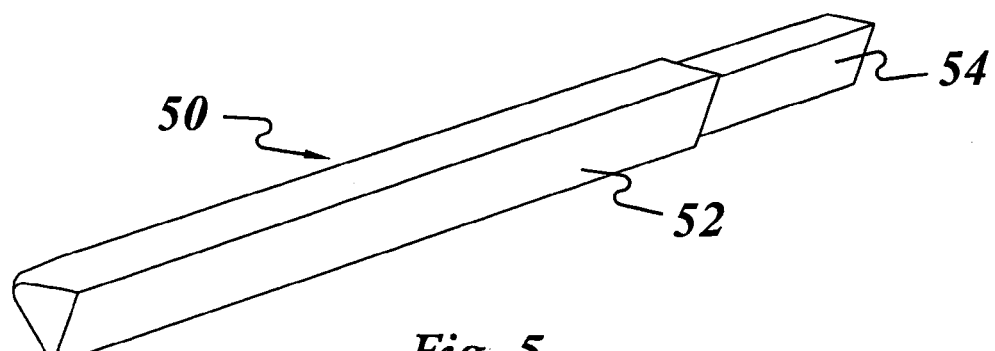
FIG. 5 is a marker which may be included in the kit shown in FIG. 1.

As shown in FIG. 5, a marker 50, which may also be included in the kit 20, has a body 52 and a cap 54. The marker is provided for marking on the labels 40 or flags 62. Preferably the marker has an ink which allows for marking on most surfaces, including skin.

Turning now to FIG. 6, one or more medication marking flag assemblies 60 are included in the kit 20. The medication marking flag assembly 60 preferably includes a colored adhesive flag 62 on a backing sheet 64, and a syringe strip 72. Typically, the kit will have flags of 1, 2, 3, 4, 5, 6, 7, or 8 different colors. A preferably rectangular or square flag section 66 of the flag 62 is joined to a cup section 68 of the flag 62 along a fold or bend line 74. Slots 70 extend inwardly from the sides of the cup section 68, adjacent to the bend line 74. The slots 70 better allow the flag section 66 to be folded over relative to the cup section 68, and to remain in the folded over position. The strip 72, preferably made of the same material as the flag 62, is also adhered to the backing sheet 64. The flag assembly may be manufactured by die-cutting or stamping of a laminate of base material having the flag material adhered to the backing sheet material. This allows the flag 62 and the strip 72 to be formed in a single manufacturing step. The flag 62 may be opaque or transparent. While FIG. 6 shows a single strip 72, two or more strips may be provided on the flag assembly. In addition to placing a strip 72 on a syringe, the strips 72 may also be placed on wires, cables or tubes in the OR. The strip 72 then helps the surgical team to identify specific cables or tubes. The strips 72 may alternatively be provided at or near the center of the cup section, as shown in dotted lines in FIG. 6.

As shown in FIG. 1, the kit is packaged or assembled in a way that reduces the potential for accidentally dropping any of the kit contents when the package 22 is opened. All kit contents are packaged in the cup 30. A band, such as a rubber band 35, is looped around the end of the marker 30, and also around the cup 30.

The sheet of printed labels 40 is folded and inserted into the cup. The flag assemblies 60 are placed into the cup with the adhesive side facing in. This tends to form the flag assemblies into a concave shape. Any tendency for a label to inadvertently peel off of a cup during use is reduced.

In use, the kit 20 is opened in the OR by tearing or cutting the package 22 open at the tear line 28. As the cup 30 is preferably visible through the package, the natural tendency is to hold the package with the cup 30 upright. Then when the package is opened, nothing falls out. This helps avoid the loss of sterility caused when an object accidentally falls to the floor as the package is opened. After the contents of the kit 20 are removed from the package 22, a flag 62 is peeled off of the backing sheet 64 of the flag assembly 60. The flag 62 is attached to a cup 30 via the adhesive back of the cup section 68. The cup section 68 has an adhesive back surface, while the flag section 66 does not. The back surface of the cup section 68 is adhered to the outside cylindrical side wall of the cup 30, as shown in FIG. 8. The cup 30 or 32 may be provided in the kit 20 or may be separately provided. The flag section 66 is then folded down, so that it partially overlies the open top end of the cup 30, as shown in FIG. 9. The marker 50 may then be used to mark the flag section 66 with the name of a drug to be used. Alternatively, a label 40 may be peeled off the backing strip 42 and applied to the flag section 66. The label 40 preferably has space so that additional information can be written onto the label by hand. In addition, one or more blank labels may be provided. The cup 30 is then clearly marked with a drug label, and preferably also with a specific color (of the flag 62).

The strip 72 is similarly peeled off of the backing sheet 64 and adhered onto a syringe 80. This provides a visual link or connection between the syringe 80 and the cup 30. A medication or drug is then poured into the cup 30. The drug is then drawn from the cup 30 into the syringe 80, as needed and administered to the patient. A second cup 32, preferably of different size from the first cup 30 is similarly labeled with a second medication flag 62, having a different color and drug label. The strip 72 from the second flag assembly 60 is similarly applied to a second syringe, to provide a visual connection or link between the contents of the second cup 32 and the second syringe. Since each cup and syringe is labeled with a flag 62 or strip 72 (with the flag 62 optionally including a label 40), the surgical team can readily determine which drug is in each syringe. Consequently, the risk of providing the wrong drug to the patient is reduced.

Thus, a novel medication labeling kit and methods have been shown and described. Various changes and substitutions may of course be made without departing from the spirit and scope of the invention. The invention, therefore, should not be limited, except by the following claims, and their equivalents.

The invention claimed is:

1. A label for medications provided in a cup, comprising:
a cup section having an adhesive back surface;
a flag section attached to the cup section at a bend line, with slots in the cup section at the bend line;
and with the flag section having a width greater than the width of the cup section;
a syringe strip having an adhesive back surface; and
with the cup section and the syringe strip on a backing sheet.

2. The label of claim 1 wherein the flag section and the cup section and the syringe strip comprise a colored transparent flexible material.

3. The label of claim 1 wherein the cup section is trapezoidal and the flag section is rectangular or square.

4. The label of claim 1 wherein the syringe strip is rectangular and has a length to width ratio greater than four.

5. The label of claim 1 wherein the syringe strip has length substantially equal to the length of the cup section.

6. The label of claim 1 wherein the adhesive back surface of the cup section and/or the syringe strip is peelably attached to a backing sheet.

7. The label of claim 1 wherein the syringe strip is separate from the flag section and the cup section.

8. The label of claim 1 with the cup section adapted to adhere to a cylindrical cup, and with the flag section adapted to be positioned at an angle relative to the cup section.

9. A label comprising:
- a cup section having an adhesive back surface, an upper end, a left side and a right side;
- a flag section attached to the upper end of the cup section, with one or more slots at the upper end of the cup section, between the cup section and the flag section;
- the flag section having a width greater than the width of the cup section;
- a syringe strip having an adhesive back surface; and
- with the cup section and the syringe strip on a backing sheet.

10. The label of claim 9 with the cup section attached to the flag section at a bend line.

* * * * *